United States Patent
Kurihara et al.

(10) Patent No.: US 9,212,377 B2
(45) Date of Patent: Dec. 15, 2015

(54) METHOD FOR PRODUCING SUGAR SOLUTION

(75) Inventors: Hiroyuki Kurihara, Kamakura (JP); Yuki Yamamoto, Kamakura (JP); Katsushige Yamada, Kamakura (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 14/002,383

(22) PCT Filed: Mar. 2, 2012

(86) PCT No.: PCT/JP2012/055323
§ 371 (c)(1),
(2), (4) Date: Aug. 30, 2013

(87) PCT Pub. No.: WO2012/118171
PCT Pub. Date: Sep. 7, 2012

(65) Prior Publication Data
US 2013/0344543 A1 Dec. 26, 2013

(30) Foreign Application Priority Data

Mar. 3, 2011 (JP) ................................. 2011-046623

(51) Int. Cl.
| | | |
|---|---|---|
| *C12P 7/64* | (2006.01) | |
| *C12P 7/10* | (2006.01) | |
| *C12P 19/14* | (2006.01) | |
| *C13K 1/02* | (2006.01) | |
| *C12P 7/06* | (2006.01) | |
| *C12P 7/56* | (2006.01) | |
| *C12P 19/02* | (2006.01) | |
| *C13B 20/16* | (2011.01) | |
| *C13K 13/00* | (2006.01) | |

(52) U.S. Cl.
CPC . *C12P 19/14* (2013.01); *C12P 7/06* (2013.01); *C12P 7/10* (2013.01); *C12P 7/56* (2013.01); *C12P 19/02* (2013.01); *C12Y 302/01004* (2013.01); *C13B 20/165* (2013.01); *C13K 1/02* (2013.01); *C13K 13/002* (2013.01); *C12P 2203/00* (2013.01); *Y02E 50/16* (2013.01); *Y02E 50/17* (2013.01)

(58) Field of Classification Search
CPC .......................... C12P 2201/00; C12P 2203/00
See application file for complete search history.

(56) References Cited

U.S. PATENT DOCUMENTS

2012/0107920 A1 5/2012 Taneda et al.

FOREIGN PATENT DOCUMENTS

| | | |
|---|---|---|
| JP | 63-087994 A | 4/1988 |
| JP | 2006-087319 A | 4/2006 |
| JP | 2008-161125 A | 7/2008 |
| JP | 2008-206484 A | 9/2008 |
| JP | 2008-535664 A | 9/2008 |
| WO | 2010/067785 A1 | 6/2010 |
| WO | 2011/007574 | 1/2011 |

OTHER PUBLICATIONS

Supplementary European Search Report of corresponding European Application No. 12752704.2 dated Sep. 4, 2014.
Chinese Office Action of corresponding Chinese Application No. 201280011279.2 dated Jun. 27, 2014 with English translation.
Yuanshan, L., "Study on Cellulase Induced by Waste Molasses of Ethanol from Trichoderma Knoningii," Mater's Thesis from Gugangxi University, May 2004 along with its English translation.

*Primary Examiner* — Maryam Monshipouri
(74) *Attorney, Agent, or Firm* — DLA Piper LLP (US)

(57) ABSTRACT

A method produces a sugar liquid by adding a filamentous fungus-derived cellulase to a pretreated product of cellulose to obtain a hydrolysate; adding waste molasses to said hydrolysate to obtain a mixed sugar liquid; and subjecting said mixed sugar liquid to solid-liquid separation and filtering the obtained solution component through an ultrafiltration membrane, to recover the filamentous fungus-derived cellulase as a non-permeate and to obtain a sugar liquid as a permeate.

20 Claims, 2 Drawing Sheets

METHOD FOR PRODUCING SUGAR SOLUTION

TECHNICAL FIELD

This disclosure relates to a method of producing a sugar liquid from biomass.

BACKGROUND

In recent years, methods of producing a sugar liquid by pretreating a cellulose-containing biomass with an acid, hot water, alkali or the like and then adding cellulase thereto to perform hydrolysis have been widely studied. However, these methods using cellulase have a drawback in that, since a large amount of cellulase is used and cellulase is expensive, the cost of producing a sugar liquid is high.

As methods of solving the problem, methods wherein the cellulase used for hydrolysis of cellulose is recovered and reused have been proposed. Disclosed examples of such methods include a method wherein continuous solid-liquid separation is carried out with a spin filter and the obtained sugar liquid is filtered through an ultrafiltration membrane to recover cellulase (JP 2006-087319 A), a method wherein a surfactant is fed at the stage of enzymatic saccharification to suppress cellulase adsorption and thereby enhance the recovery efficiency (JP 63-087994 A) and a method wherein the residue produced by enzymatic saccharification is subjected to electric treatment to recover the cellulase component (JP 2008-206484 A), but these methods failed to fundamentally solve the problem.

There is thus a need to reduce the amount of cellulase used in hydrolysis of cellulose.

SUMMARY

We focused our attention on adding waste molasses to cellulose hydrolysate. As a result, we discovered that this improves the amount of cellulase recovered from the cellulose hydrolysate.

We thus provide:

[1] A method of producing a sugar liquid, the method comprising the Steps (1) to (3) below:
Step (1): a step of adding a filamentous fungus-derived cellulase to a pretreated product of cellulose to obtain a hydrolysate;
Step (2): a step of adding waste molasses to the hydrolysate to obtain a mixed sugar liquid; and
Step (3): a step of subjecting the mixed sugar liquid to solid-liquid separation and filtering the obtained solution component through an ultrafiltration membrane, to recover the filamentous fungus-derived cellulase as a non-permeate and to obtain a sugar liquid as a permeate.

[2] The method of producing a sugar liquid according to [1], wherein the filamentous fungus-derived cellulase of Step (1) is *Trichoderma*-derived cellulase.

[3] The method of producing a sugar liquid according to [1] or [2], wherein the pretreated product of cellulose of Step (1) is one or more products selected from the group consisting of products obtained by hydrothermal treatment, dilute sulfuric acid treatment or alkali treatment.

[4] The method of producing a sugar liquid according to any one of [1] to [3], wherein, in Step (2), waste molasses is added to the hydrolysate to prepare a mixed sugar liquid whose sugar concentration is within the range of 50 to 200 g/L.

[5] The method of producing a sugar liquid according to any one of [1] to [4], wherein Step (2) comprises a process of incubating the mixed sugar liquid at a temperature within the range of 40 to 60° C.

[6] The method of producing a sugar liquid according to any one of [1] to [5], the method comprising the step of filtering the sugar liquid of Step (3) through a nanofiltration membrane and/or reverse osmosis membrane to remove fermentation inhibitors as a permeate and to obtain a sugar concentrate as a non-permeate.

[7] A method of producing a chemical product, the method comprising performing fermentation culture of a microorganism having a capacity to produce a chemical product using, as a fermentation feedstock, a sugar liquid obtained by the method for producing a sugar liquid according to any one of [1] to [6].

With our methods, the enzyme recovery of filamentous fungus-derived cellulase from a cellulose hydrolysate is improved so that the amount of cellulase used in the process of producing a sugar liquid can be reduced. Further, by adding waste molasses to the cellulose hydrolysate to prepare a mixed sugar liquid, sugar components can be recovered not only from cellulose but also from the waste molasses.

DESCRIPTION OF SYMBOLS

Figure 1:
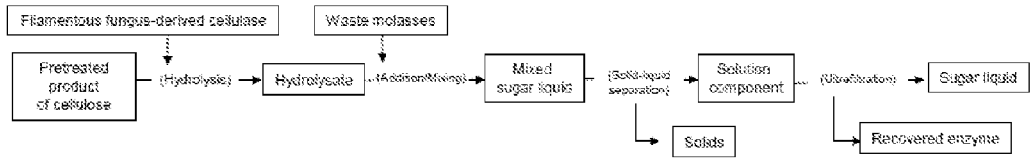
FIG. 1 is a schematic flow diagram showing the steps of an example of our method.

1 Incubator
2 Hydrolysis tank
3 Mixer
4 Liquid sending pump
5 Solid-liquid separator
6 Microfiltration membrane device
7 Solution collection tank
8 Ultrafiltration membrane pump
9 Ultrafiltration membrane
10 Sugar liquid collection tank
11 High-pressure pump
12 Nanofiltration membrane and/or reverse osmosis membrane
13 Incubator
14 Fermenter
15 Stirrer
16 Microorganism separation device
17 Shredder
18 Squeezer
19 Juice tank
20 Effect evaporator
21 Crystallizer
22 Separation device
23 Transporter
24 Pulverizer 25 Heater
26 Transportation line

DETAILED DESCRIPTION

Examples are described below in detail for each Step.

Step (1)

The pretreated product of cellulose in Step (1) means a cellulose-containing biomass that was pretreated for hydrolysis. Specific examples of the cellulose-containing biomass include herbaceous biomasses such as bagasse, switchgrass, napier grass, *Erianthus*, corn stover, rice straw and wheat straw; woody biomasses such as trees and waste building materials; and water environment-derived biomasses such as algae and seaweeds. Such biomasses contain, in addition to cellulose and hemicellulose (hereinafter referred to as "cellulose" as a general term for cellulose and hemicellulose), lignin as aromatic macromolecules, and the like. In particular, pretreatment of a cellulose-containing biomass is carried out to improve the efficiency of hydrolysis of the biomass by filamentous fungus-derived cellulase, and the product obtained as a result is referred to as a pretreated product of cellulose.

Examples of the pretreatment include acid treatment, sulfuric acid treatment, dilute sulfuric acid treatment, alkali treatment, hydrothermal treatment, subcritical water treatment, pulverization treatment, steaming treatment and drying treatment. The pretreatment is preferably hydrothermal treatment, dilute sulfuric acid treatment or alkali treatment since alkali treatment, hydrothermal treatment and dilute sulfuric acid treatment show better enzymatic saccharification efficiencies and require smaller amounts of enzyme compared to other methods.

In the case of hydrothermal treatment, water is added such that the concentration of cellulose-containing biomass is 0.1 to 50% by weight, and the resulting mixture is treated at a temperature of 100 to 400° C. for 1 second to 60 minutes. By treatment under such a temperature condition, a pretreated product of cellulose that can be easily hydrolyzed by cellulase can be obtained. The number of times of the treatment is not restricted, and 1 or more times of the treatment may be carried out. In particular, in cases where the treatment is carried out 2 or more times, the conditions for the first treatment may be different from those for the second and later treatments.

In the case of dilute sulfuric acid treatment, the concentration of sulfuric acid is preferably 0.1 to 15% by weight, more preferably 0.5 to 5% by weight. The reaction temperature may be set at 100 to 300° C., and is preferably set at 120 to 250° C. The reaction time may be set at 1 second to 60 minutes. The number of times of the treatment is not restricted, and 1 or more times of the treatment may be carried out. In particular, in cases where the treatment is carried out 2 or more times, the conditions for the first treatment may be different from those for the second and later treatments. Since the hydrolysate obtained by dilute sulfuric acid treatment contains an acid, neutralization is necessary to further carry out hydrolysis reaction with cellulase or to use the hydrolysate as a fermentation feedstock.

The alkali treatment is a method wherein an alkali selected from sodium hydroxide, calcium hydroxide and ammonia is allowed to act on a cellulose-containing biomass. As the alkali to be used in the alkali treatment, ammonia may be especially preferably used. The ammonia treatment may be carried out by methods described in JP 2008-161125 A and JP 2008-535664 A. For example, ammonia is added at a concentration of 0.1 to 15% by weight to a cellulose-containing biomass, and the treatment is carried out at 4 to 200° C., preferably 90 to 150° C. The ammonia to be added may be in the state of either liquid or gas. Further, the form of the ammonia to be added may be either pure ammonia or aqueous ammonia. The number of times of the treatment is not restricted, and 1 or more times of the treatment may be carried out. In particular, in cases where the treatment is carried out 2 or more times, the conditions for the first treatment may be different from those for the second and later treatments. The treated product obtained by ammonia treatment needs to be subjected to neutralization of ammonia or removal of ammonia to further carry out enzymatic hydrolysis reaction. The neutralization of ammonia may be carried out either after removal of the solid component from the hydrolysate by solid-liquid separation or in a state where the solid component is contained. The acid reagent to be used for neutralization is not restricted. For removal of ammonia, the ammonia-treated product may be kept under reduced pressure to allow evaporation of ammonia into the gas state. The removed ammonia may be recovered and reused.

In Step (1), the pretreated product of cellulose described above is subjected to hydrolysis with cellulase to obtain a hydrolysate. The hydrolysis of cellulose means to decrease the molecular weight of cellulose. Further, in the hydrolysis of cellulose, hemicellulose components such as xylan, mannan and arabinan are hydrolyzed at the same time. Examples of monosaccharide components contained in the hydrolysate include glucose, xylose, mannose and galactose, and the major monosaccharide component is glucose, which is a hydrolysate of cellulose. Further, in cases where the hydrolysis is insufficient, disaccharides such as cellobiose and xylobiose; cello-oligosaccharides; xylo-oligosaccharides; and the like are contained.

In Step (1), the pretreated product of cellulose is hydrolyzed with a filamentous fungus-derived cellulase. Examples of the filamentous fungus-derived cellulase include those derived from *Trichoderma, Aspergillus, Cellulomonas, Clostridium, Streptomyces, Humicola, Acremonium, Irpex, Mucor, Talaromyces, Phanerochaete*, white-rot fungi and brown-rot fungi. Among such filamentous fungus-derived cellulases, *Trichoderma*-derived cellulase, which has high cellulose-degrading activity, is preferably used.

The *Trichoderma*-derived cellulase is an enzyme composition comprising cellulase derived from a microorganism belonging to the genus *Trichoderma* as a major component. The microorganism belonging to the genus *Trichoderma* is not restricted, and is preferably *Trichoderma reesei*. Specific examples of such a microorganism include *Trichoderma reesei* QM9414, *Trichoderma reesei* QM9123, *Trichoderma reesei* Rut C-30, *Trichoderma reesei* PC3-7, *Trichoderma reesei* CL-847, *Trichoderma reesei* MCG77, *Trichoderma reesei* MCG80 and *Trichoderma viride* QM9123. The cellulase may also be derived from a mutant strain originated from the above-described *Trichoderma* microorganism, which mutant strain was prepared by mutagenesis using a mutagen, UV irradiation or the like to enhance the cellulase productivity.

The *Trichoderma*-derived cellulase is an enzyme composition that comprises a plurality of enzyme components such as cellobiohydrolase, endoglucanase, exoglucanase, β-glucosidase, xylanase and xylosidase, which enzyme composition has an activity to hydrolyze cellulose to cause saccharification. In cellulose degradation, the *Trichoderma*-derived cellulase has a coordinate effect or complementary effect by the plurality of enzyme components, and enables more efficient hydrolysis of cellulose thereby. The cellulase especially preferably comprises *Trichoderma*-derived cellobiohydrolase and xylanase.

Cellobiohydrolase is a general term for cellulases that hydrolyze cellulose from the terminal portions. The group of enzymes belonging to cellobiohydrolase are described as EC number: EC3.2.1.91.

Endoglucanase is a general term for cellulases that hydrolyze cellulose molecular chains from their central portions. The group of enzymes belonging to endoglucanase are described as EC numbers: EC3.2.1.4, EC3.2.1.6, EC3.2.1.39 and EC3.2.1.73.

Exoglucanase is a general term for cellulases that hydrolyze cellulose molecular chains from their termini. The group of enzymes belonging to exoglucanase are described as EC numbers: EC3.2.1.74 and EC3.2.1.58.

β-glucosidase is a general term for cellulases that act on cello-oligosaccharides or cellobiose. The group of enzymes belonging to β-glucosidase are described as EC number: EC3.2.1.21.

Xylanase is a general term for cellulases that act on hemicellulose or, especially, xylan. The group of enzymes belonging to xylanase are described as EC number: EC3.2.1.8.

Xylosidase is a general term for cellulases that act on xylo-oligosaccharides. The group of enzymes belonging to xylosidase are described as EC number: EC3.2.1.37.

As the *Trichoderma*-derived cellulase, a crude enzyme product is preferably used. The crude enzyme product is derived from a culture supernatant obtained by culturing a *Trichoderma* microorganism for an arbitrary period in a medium prepared such that the microorganism produces cellulase. The medium components to be used are not restricted, and a medium supplemented with cellulose to promote production of cellulase may be generally used. As the crude enzyme product, the culture liquid may be used as it is, or a culture supernatant processed only by removal of *Trichoderma* cells is preferably used.

The weight ratios of enzyme components in the crude enzyme product are not restricted. For example, a culture liquid derived from *Trichoderma reesei* contains 50 to 95% by weight cellobiohydrolase, and also contains as other components endoglucanase, β-glucosidase and the like. While microorganisms belonging to *Trichoderma* produce strong cellulase components into the culture liquid, the β-glucosidase activity in the culture liquid is low since β-glucosidase is retained in the cells or on the cell surfaces. Therefore, β-glucosidase from a different species or from the same species may be added to the crude enzyme product. As the β-glucosidase from a different species, β-glucosidase derived from *Aspergillus* may be preferably used. Examples of the β-glucosidase derived from *Aspergillus* include Novozyme 188, which is commercially available from Novozyme. The method of addition of β-glucosidase from a different species or from the same species to the crude enzyme product may also be a method wherein a gene is introduced to a microorganism belonging to *Trichoderma* to perform genetic recombination of the microorganism such that β-glucosidase is produced into the culture liquid, and the microorganism belonging to *Trichoderma* is then cultured, followed by isolating the culture liquid.

The reaction temperature for hydrolysis with the filamentous fungus-derived cellulase is preferably 15 to 100° C., more preferably 40 to 60° C., most preferably 50° C. The pH for the hydrolysis reaction is preferably pH 3 to 9, more preferably pH 4 to 5.5, most preferably pH 5. To adjust the pH, an acid or alkali may be added such that a desired pH is achieved. Further, as required, a buffer may be used.

In addition, in the hydrolysis of a pretreated product of cellulose, stirring/mixing is preferably carried out to promote contacting between the pretreated product of cellulose and the filamentous-fungal cellulase, and to achieve a uniform sugar concentration in the hydrolysate. The solid concentration of the pretreated product of cellulose is more preferably 1 to 25% by weight. In particular, in Step (1), the solid concentration of the pretreated product of cellulose is preferably set as low as 2 to 10% by weight. This aims to secure a sufficient amount of liquid for diluting waste molasses in the Step (2) at a later stage. Another advantage of setting the solid concentration as low as 2 to 10% by weight is improvement of the efficiency of hydrolysis of the pretreated product of cellulose. This is due to the property of filamentous fungus-derived cellulase that the enzyme reaction is inhibited by sugar products such as glucose and cellobiose, which are products produced by the hydrolysis.

The sugar concentration in the hydrolysate obtained in Step (1) is not limited, and is preferably 10 to 100 g/L, more preferably 20 to 80 g/L in terms of the monosaccharide concentration. This is because a sugar concentration within this range allows adjustment of the sugar concentration to the most appropriate value upon mixing with waste molasses at a later stage.

Step (2)

Waste molasses is added to the hydrolysate obtained in the Step (1) described above. The waste molasses (Morasess) means a by-product produced in the process of manufacturing sugar from juice of a sugar crop such as sugar cane, sugar beet, *Beta vulgaris*, beet or grape, or from raw sugar prepared by once crystallizing such juice of a sugar crop. The waste molasses is a solution containing sugar components that remained after the sugar crystallization step in the sugar manufacturing process. In general, the sugar crystallization step is normally carried out a plurality of times such that a first sugar is produced as a crystalline component obtained by the first crystallization, a second sugar is produced as a crystalline component obtained by crystallizing the residual liquid of the first sugar (first molasses), a third sugar is produced by crystallizing the residual liquid of the second sugar (second molasses), and the step is further repeated. The final molasses obtained as a residual liquid is called waste molasses. The sugar components contained in waste molasses are mainly sucrose, glucose and fructose, and certain amounts of other sugar components such as xylose and galactose may also be contained therein. As the number of times of crystallization increases, the concentrations of components other than sugar components derived from the sugar crop increase in the waste molasses. Thus, waste molasses is known to also contain a large amount of fermentation inhibitors. Examples of the fermentation inhibitors contained in waste molasses include acetic acid, formic acid, hydroxymethylfurfural, furfural, vanillin, acetovanillone, guaiacol and various inorganic substances (ions). However, components and the amounts of sugars and fermentation inhibitors contained in the waste molasses are not limited.

The waste molasses used in Step (2) is preferably molasses obtained after many times of crystallization. More specifically, the waste molasses is one that remained after repeating crystallization preferably not less than 2 times, more preferably not less than 3 times. Further, the sugar concentration in the waste molasses is preferably not less than 200 g/L, more preferably not less than 500 g/L. In cases where the sugar component concentration in the waste molasses is less than 200 g/L, the recovery of filamentous fungus-derived cellulase does not increase, which is not preferred. On the other hand, although the upper limit of the sugar component concentration in the waste molasses used in Step (2) is not limited, the upper limit of the sugar component concentration in waste molasses obtained by a normal sugar manufacturing process is considered to be 800 g/L. The sugar concentration in waste molasses can be measured using a known measurement method such as HPLC. Further, the waste molasses preferably contains $K^+$ ions in addition to the above-described sugars. The concentration of $K^+$ ions in the waste molasses preferably used is not less than 1 g/L, more preferably not less than 5 g/L, most preferably not less than 10 g/L.

The waste molasses is added to the hydrolysate of Step (1) to prepare a mixed sugar liquid. The sugar concentration in the mixed sugar liquid is preferably not more than 200 g/L, more preferably not more than 150 g/L since, in cases where the sugar concentration in the mixed sugar liquid is too high, the viscosity is too high, so that the flux in the later ultrafiltration membrane treatment may be low. On the other hand, in cases where the sugar concentration in the mixed sugar liquid is less than 40 g/L, the concentration of the sugar liquid finally obtained may be low, so that the sugar concentration in the mixed sugar liquid is preferably not less than 40 g/L, more preferably not less than 50 g/L. That is, the waste molasses is added such that the sugar concentration in the mixed sugar liquid is preferably 40 to 200 g/L, more preferably 50 to 150 g/L. Although the mixed sugar liquid may be incubated at room temperature (25° C.), the liquid is preferably incubated at a temperature of 40 to 60° C., more preferably incubated at a temperature of about 50° C. By this, the amount of enzyme that can be recovered with an ultrafiltration membrane in a later step increases, which is preferred.

Some types of microorganisms to be used for fermentation have low efficiency of utilization of sucrose, which is a major sugar in waste molasses, as a carbon source. Thus, in cases where waste molasses is used as a fermentation feedstock in production of a chemical product using such a microorganism, it is preferred to hydrolyze sucrose contained in the waste molasses into glucose and fructose in advance. The hydrolysis treatment of waste molasses may also be heat treatment under acidic or alkaline conditions. Further, enzyme treatment with invertase, sucrase and/or the like may be carried out. Invertase is also called β-fructofuranosidase, and means an enzyme that hydrolyzes sucrose into glucose and fructose. Sucrase also means an enzyme that hydrolyzes sucrose into glucose and fructose. The invertase used is not limited, and the yeast-derived invertase commercially available from Biocon (Japan) Ltd. or Mitsubishi-Kagaku Foods Corporation may be purchased and used. The treatment conditions for invertase may be those normally used for its efficient action. The sucrase to be used is also not limited, and the sucrase commercially available from Wako Pure Chemical Industries, Ltd. or Mitsubishi-Kagaku Foods Corporation may be purchased and used. The treatment conditions for sucrase may be those normally used for its efficient action. The invertase or sucrase treatment may be carried out by adding invertase or sucrase in advance to the waste molasses alone, or may be carried out after preparation of the mixed sugar liquid by addition of the waste molasses to the hydrolysate of Step (1). Since, as described above, incubation of the mixed sugar liquid at a temperature of 40 to 60° C. increases the amount of enzyme recovered, hydrolysis reaction of sucrose can also be carried out by adding invertase or sucrase in this process.

Step (3)

In Step (3), the mixed sugar liquid obtained in Step (2) is subjected to solid-liquid separation, and the solution component is recovered. The solid-liquid separation can be carried out by a known solid-liquid separation method such as: centrifugation using a screw decanter or the like; filtration including pressure/suction filtration; or membrane filtration including microfiltration. Such solid-liquid separation may also be carried out by a combination of more than one method, and is not restricted as long as solids can be efficiently removed thereby. However, in view of suppression of fouling of an ultrafiltration membrane at a later stage, the solution component after the solid-liquid separation is preferably solid-free as much as possible, and, more specifically, it is preferred to carry out first solid-liquid separation by centrifugation or by filtration using a filter press or the like, followed by further subjecting the obtained solution component to membrane filtration through a microfiltration membrane to completely remove solids. A microfiltration membrane is also called membrane filtration, and is a separation membrane that can separate and remove particles having a size of about 0.01 to 10 μm from a particulate suspension using a pressure difference as a driving force. A microfiltration membrane has pores having a size of 0.01 to 10 μm on its surface, and particulate components larger than the pores can be separated/removed to the membrane side. Examples of the material of a microfiltration membrane include, but are not limited to, cellulose acetate, aromatic polyamide, polyvinyl alcohol, polysulfone, polyvinylidene fluoride, polyethylene, polyacrylonitrile, ceramics, polypropylene, polycarbonate and polytetrafluoroethylene (Teflon (registered trademark)). The membrane is preferably a polyvinylidene fluoride microfiltration membrane in view of contamination resistance, chemical resistance, strength, filtration performance and the like.

Subsequently, the solution component is subjected to ultrafiltration membrane treatment. An ultrafiltration membrane generally means a separation membrane that has a pore size of 1.5 nanometers to 250 nanometers and can block water-soluble macromolecules having molecular weights of 1,000 to 200,000 as a non-permeate. The molecular weight cut off of the ultrafiltration membrane is not limited as long as filamentous fungus-derived cellulase can be recovered, and the molecular weight cut off is preferably 1,000 to 100,000 Da, more preferably 10,000 to 30,000 Da. Examples of the material of the ultrafiltration membrane that may be used include polyether sulfone (PES), polyvinylidene fluoride (PVDF) and regenerated cellulose, and, since cellulose is degraded by filamentous fungus-derived cellulase, the material of the ultrafiltration membrane is preferably a synthetic polymer such as PES or PVDF. Preferred examples of the shape of the ultrafiltration membrane include a tubular type, a spiral element and a flat membrane. Examples of the mode of filtration through the ultrafiltration membrane include cross-flow filtration and dead-end filtration, and, in view of fouling and the flux, cross-flow filtration is preferred.

By filtering the solution component through the ultrafiltration membrane, a sugar liquid can be obtained as a permeate. The sugar liquid obtained is a liquid produced by almost complete removal of the solids that have been originally contained in the mixed sugar liquid by solid-liquid separation. On the other hand, by filtration through the ultrafiltration membrane, colored substances and water-soluble macromolecules in the mixed sugar liquid are removed into the non-permeate side, which water-soluble macromolecules contain the filamentous fungus-derived cellulase component used in Step (1). The filamentous fungus-derived cellulase component to be recovered is not limited, and the whole or a part of the filamentous fungus-derived cellulase component used in the hydrolysis can be recovered as the non-permeate. Since the non-permeate also contains sugar components derived from the mixed sugar liquid, an operation of adding water to the non-permeate and further filtering the resultant through an ultrafiltration membrane may be repeated to recover such sugar components.

Step (3) has an effect to remarkably increase the enzyme amount of filamentous fungus-derived cellulase contained in the recovered enzyme as compared to conventional techniques and, among the filamentous fungus-derived cellulase components, cellobiohydrolase and xylanase are recovered especially at high efficiency. By reusing the recovered filamentous fungus-derived cellulase for hydrolysis of the pretreated product of cellulose, the amount of the filamentous fungus-derived cellulase to be used can be reduced. The recovered filamentous fungus-derived cellulase may be reused alone for the hydrolysis, or may be reused after being mixed with fresh filamentous fungus-derived cellulase. Further, in some cases, the recovered filamentous fungus-derived cellulase may be effectively utilized in a use other than hydrolysis of cellulose.

Sugar Concentration Step

By filtering, as in the method described in WO 2010/067785, the sugar liquid obtained in Step (3) through a nanofiltration membrane and/or reverse osmosis membrane, a concentrated sugar liquid containing concentrated sugar components can be obtained as a non-permeate.

A nanofiltration membrane is also called a nanofilter (nanofiltration membrane, NF membrane), and generally defined as a "membrane that allows permeation of monovalent ions, but blocks divalent ions." The membrane is considered to have fine voids having sizes of about several nanometers, and mainly used to block fine particles, molecules, ions, salts and the like in water.

A reverse osmosis membrane is also called an RO membrane, and generally defined as a "membrane having a desalting function also for monovalent ions." The membrane is considered to have ultrafine voids having sizes of about several angstroms to several nanometers, and mainly used for removal of ion components such as seawater desalination and ultrapure water production.

Examples of the material of the nanofiltration membrane or reverse osmosis membrane that may be used include polymer materials such as cellulose acetate polymers, polyamides, polyesters, polyimides, vinyl polymers and polysulfones. The membrane is not limited to a membrane constituted by one of the materials, and may be a membrane comprising a plurality of the membrane materials.

As the nanofiltration membrane to be used, a spiral-wound membrane element is preferred. Specific examples of preferred nanofiltration membrane elements include a cellulose acetate nanofiltration membrane element GE Sepa, manufactured by GE Osmonics; nanofiltration membrane elements NF99 and NF99HF, manufactured by Alfa-Laval, which have polyamide functional layers; nanofiltration membrane elements NF-45, NF-90, NF-200, NF-270 and NF-400, manufactured by FilmTec Corporation, which have cross-linked piperazine polyamide functional layers; and nanofiltration membrane elements SU-210, SU-220, SU-600 and SU-610, manufactured by Toray Industries, Inc., comprising a nanofiltration membrane UTC60, manufactured by the same manufacturer, which comprises a cross-linked piperazine polyamide as a major component. The nanofiltration membrane element is more preferably NF99 or NF99HF; NF-45, NF-90, NF-200 or NF-400; or SU-210, SU-220, SU-600 or SU-610. The nanofiltration membrane element is still more preferably SU-210, SU-220, SU-600 or SU-610.

In terms of the material of the reverse osmosis membrane used, examples of the membrane include a composite membrane comprising a cellulose acetate polymer as a functional layer (hereinafter referred to as cellulose acetate reverse osmosis membrane) and a composite membrane comprising a polyamide as a functional layer (hereinafter referred to as polyamide reverse osmosis membrane). Examples of the cellulose acetate polymer herein include polymers prepared with organic acid esters of cellulose such as cellulose acetate, cellulose diacetate, cellulose triacetate, cellulose propionate and cellulose butyrate, which may be used alone, as a mixture, or as a mixed ester. Examples of the polyamide include linear polymers and cross-linked polymers composed of aliphatic and/or aromatic diamine monomers.

Specific examples of the reverse osmosis membrane used include polyamide reverse osmosis membrane modules manufactured by TORAY INDUSTRIES, INC., SUL-G10 and SUL-G20, which are ultralow-pressure type modules, and SU-710, SU-720, SU-720F, SU-710L, SU-720L, SU-720LF, SU-720R, SU-710P and SU-720P, which are low-pressure type modules, as well as SU-810, SU-820, SU-820L and SU-820FA, which are high-pressure type modules containing UTC80 as a reverse osmosis membrane; cellulose acetate reverse osmosis membranes manufactured by the same manufacturer, SC-L100R, SC-L200R, SC-1100, SC-1200, SC-2100, SC-2200, SC-3100, SC-3200, SC-8100 and SC-8200; NTR-759HR, NTR-729HF, NTR-70SWC, ES10-D, ES20-D, ES20-U, ES15-D, ES15-U and LF10-D, manufactured by Nitto Denko Corporation; RO98pHt, RO99, HR98PP and CE4040C-30D, manufactured by Alfa-Laval; GE Sepa, manufactured by GE; BW30-4040, TW30-4040, XLE-4040, LP-4040, LE-4040, SW30-4040 and SW30HRLE-4040, manufactured by FilmTec Corporation; TFC-HR and TFC-ULP, manufactured by KOCH; and ACM-1, ACM-2 and ACM-4, manufactured by TRISEP.

Concentrating the sugar liquid using a nanofiltration membrane and/or reverse osmosis membrane has an advantage that the sugar concentration in the sugar liquid can be increased and fermentation inhibitors can be removed as a permeate. The term "fermentation inhibitors" herein means components, other than sugars, that inhibit fermentation in the fermentation step at a later stage, and specific examples of the fermentation inhibitors include aromatic compounds, furan compounds, organic acids and monovalent inorganic salts. Representative examples of such aromatic compounds and furan compounds include furfural, hydroxymethylfurfural, vanillin, vanillic acid, syringic acid, coniferyl aldehyde, coumaric acid and ferulic acid. Examples of the organic acids and inorganic salts include acetic acid, formic acid, potassium and sodium. The sugar concentration in the concentrated sugar liquid may be arbitrary set within the range of 50 g/L to 400 g/L depending on the treatment conditions for the nanofiltration membrane and/or the reverse osmosis membrane, and may be arbitrary set depending on the use of the concentrated sugar liquid and/or the like. In cases where more complete removal of the fermentation inhibitors is required, water may be added to the sugar liquid or the concentrated sugar liquid, followed by concentrating the resultant through a nanofiltration membrane and/or a reverse osmosis membrane to a desired sugar concentration. By this, fermentation inhibitors can be removed as a permeate.

Use of a nanofiltration membrane is more preferred since it has higher effect of removing fermentation inhibitors than a reverse osmosis membrane. Whether to use a nanofiltration membrane or to use a reverse osmosis membrane may be selected in consideration of the concentration of fermentation inhibitors contained in the mixed sugar liquid, or of how the fermentation at a later stage is influenced by the fermentation inhibitors.

The above-described concentrated sugar liquid may be further concentrated by use of a vacuum evaporator, multieffect evaporator, freeze dryer, spray dryer, hot air dryer and/or the like.

Sugar Liquid/Concentrated Sugar Liquid

Sugar liquids and/or concentrated sugar liquids obtained by methods can be used for uses such as foods, sweeteners, feeds and fermentation feedstocks.

Process of Producing Chemical Product

By using the sugar liquid and/or concentrated sugar liquid obtained by our methods as a fermentation feedstock to grow microorganisms having capacity to produce chemical products, various chemicals can be produced. "Growing microorganisms using the sugar liquid and/or concentrated sugar liquid as a fermentation feedstock" herein means that sugar components or amino sources contained in the sugar liquid are used as nutrients for microorganisms, to cause, and to allow continuation of, growth of the microorganisms. Specific examples of the chemical products include alcohols, organic acids, amino acids and nucleic acids, which are substances mass-produced in the fermentation industry. Such chemical products are produced and accumulated inside and outside the living body by using sugar components contained in the sugar liquid as carbon sources to be metabolized. Specific examples the chemical products that can be produced by the microorganisms include alcohols such as ethanol, 1,3-propanediol, 1,4-propanediol and glycerol; organic acids such as acetic acid, lactic acid, pyruvic acid, succinic acid, malic acid, itaconic acid and citric acid; nucleosides such as inosine and guanosine; nucleotides such as inosinic acid and guanylic acid; and amine compounds such as cadaverine. Further, the sugar liquid can be applied to production of enzymes, antibiotics, recombinant proteins and the like. The microorganism used for production of such a chemical product is not limited as long as the microorganism is capable of efficiently producing the chemical product of interest, and examples of the microorganism that may be used include microorganisms such as *E. coli*, yeasts, filamentous fungi and Basidiomycetes.

In cases where the sugar liquid and/or concentrated sugar liquid is/are used as the fermentation feedstock for production of a chemical product, a nitrogen source(s) and/or inorganic salt(s) may be added thereto if necessary, and an organic micronutrient(s) such as an amino acid(s) and/or vitamin(s) may be added thereto if necessary. Further, in some cases, the sugar liquid and/or concentrated sugar liquid may be supplemented with xylose and/or another/other carbon source(s) to prepare the fermentation feedstock, and examples of the carbon source(s) include sugars such as glucose, sucrose, fructose, galactose and lactose; saccharified-starch liquids containing these sugars; sweet potato molasses; sugar beet molasses; and high-test molasses; and further, organic acids such as acetic acid; alcohols such as ethanol; and glycerin. Examples of the nitrogen source(s) that may be used include ammonia gas; aqueous ammonia; ammonium salts; urea; nitrates; and other secondarily used organic nitrogen sources such as oil cakes, soybean hydrolysates, casein digests, other amino acids, vitamins, corn steep liquor, yeasts or yeast extracts, meat extracts, peptides such as peptone, and cells of various fermentation microorganisms and their hydrolysates. Examples of the inorganic salt(s) that may be added as appropriate include phosphates, magnesium salts, calcium salts, iron salts and manganese salts.

Examples of the method of culturing the microorganism include known fermentation culture methods such as batch culture, fed-batch culture and continuous culture. In particular, since solids are completely removed from the sugar liquid and/or concentrated sugar liquid using an ultrafiltration membrane and/or the like, it is possible to separate and collect the microorganism used for the fermentation by a method such as centrifugation or membrane separation, to reuse the microorganism. In such separation/collection and reuse of the microorganism, the microorganism may be continuously separated/collected while fresh sugar liquid and/or concentrated sugar liquid is/are added during the culture, or the microorganism may be separated/collected after completion of the culture to be reused for culturing the next batch.

Constitution of Sugar Liquid Manufacturing Apparatus

The method for producing a sugar liquid is described below focusing on the apparatus used therefor, with reference to schematic drawings.

FIG. 1 is a schematic flow diagram showing an example of the steps of our method. Its details are as described above.

Figure 2:
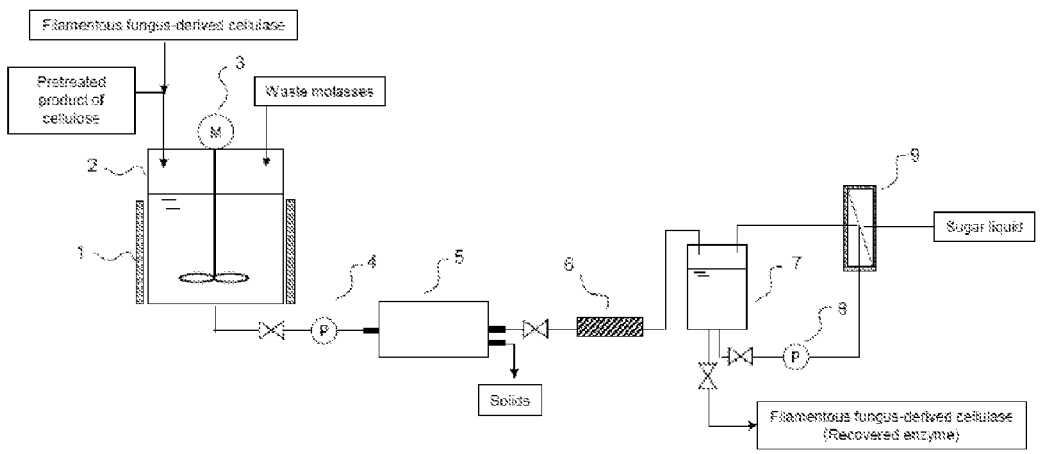
FIG. 2 is a schematic diagram of an apparatus for carrying out our methods.

FIG. 2 is a schematic diagram of an apparatus for carrying out our method. A pretreated product of cellulose and a filamentous fungus-derived cellulase are fed to a hydrolysis reaction tank (2), where hydrolysis is carried out. For efficiently performing hydrolysis, the hydrolysis tank (2) preferably comprises an incubator (1) and a mixer (3). After completion of the hydrolysis, waste molasses is fed to the hydrolysis reaction tank (2). The waste molasses to be fed may be one preliminarily diluted in consideration of ease of handling. After the addition of waste molasses to the hydrolysate, the resulting mixture is preferably mixed using the mixer (3). To increase the recovery efficiency of the filamentous fungus-derived cellulase, the incubator (1) may be used for keeping the hydrolysis tank temperature within the range of 40 to 60° C. Thereafter, the mixed sugar liquid prepared in the hydrolysis tank (2) is fed to a solid-liquid separator (5) using liquid transfer means such as a liquid sending pump (4). As the solid-liquid separator (5), a known solid-liquid separator such as a centrifuge, press filter, screw press, rotary drum filter or belt filter may be used. The solid-liquid separation is preferably carried out by filtration using a separation membrane. The solution component obtained using the solid-liquid separator (5) may be further filtered through a microfiltration membrane device (6). Thus, in the solid-liquid separation process, the solution component obtained through the solid-liquid separator (5) and the microfiltration membrane device (6) is collected in a solution collection tank (7). The solution collection tank (7) is connected via an ultrafiltration membrane pump (8) to an ultrafiltration membrane (9), where the above solution component is separated into filamentous fungus-derived cellulase and a sugar liquid. The ultrafiltration membrane (9) is preferably one processed into the shape of a module such as a spiral module. The filamentous fungus-derived cellulase separated through the ultrafiltration membrane (9) is collected as a non-permeate via the solution collection tank (7). On the other hand, the permeate of the ultrafiltration membrane (9) can be collected as a sugar liquid, and may be used for production of a chemical product or the like.

Figure 3:
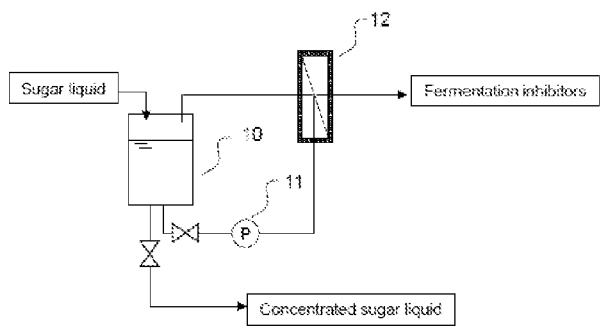
FIG. 3 is a schematic diagram of an apparatus that produces a concentrated sugar liquid.

FIG. 3 is a schematic diagram of an apparatus to further concentrate the sugar liquid. The sugar liquid is retained in a sugar liquid collection tank (10) which is connected via a high-pressure pump (11) to a nanofiltration membrane and/or reverse osmosis membrane (12). The sugar component is collected as a non-permeate of the nanofiltration membrane and/or reverse osmosis membrane (12), and collected as a concentrated sugar liquid in the sugar liquid collection tank (10). As a permeate of the nanofiltration membrane and/or reverse osmosis membrane (12), fermentation inhibitors are removed together with excess water.

Figure 4:
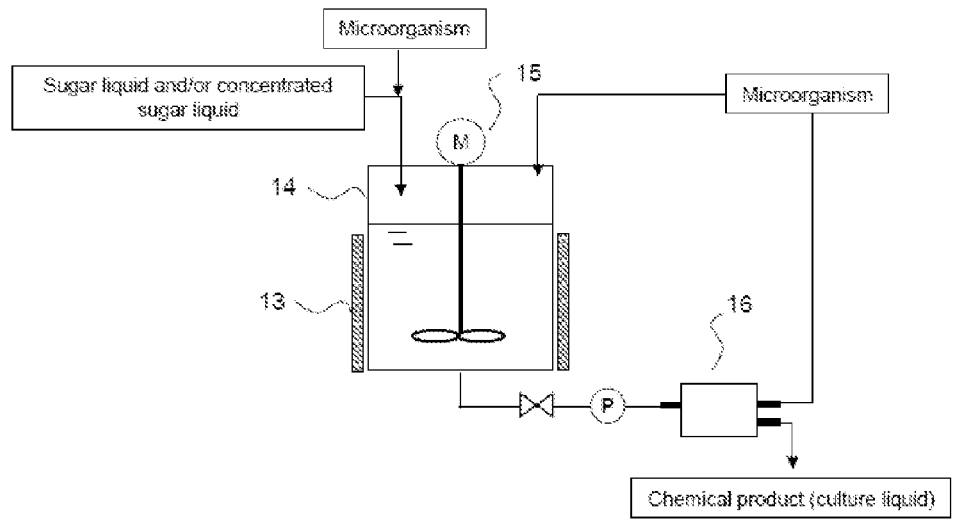
FIG. 4 is a schematic diagram showing production of a chemical product using a sugar liquid and/or concentrated sugar liquid as a fermentation feedstock.

FIG. 4 is a schematic diagram showing an apparatus that produces a chemical product using the sugar liquid and/or concentrated sugar liquid of our method. The sugar liquid and/or concentrated sugar liquid of our methods is fed to a fermenter (14) comprising a stirrer (15) and an incubator (13).

A microorganism is fed to, and grown in, the fermenter to produce a chemical product, while the microorganism can be separated by a microorganism separation device (16) from the culture liquid comprising the chemical product upon completion of the culture or during the culture process. The microorganism separated by the microorganism separation device (16) is collected in the fermenter (14).

Figure 5:
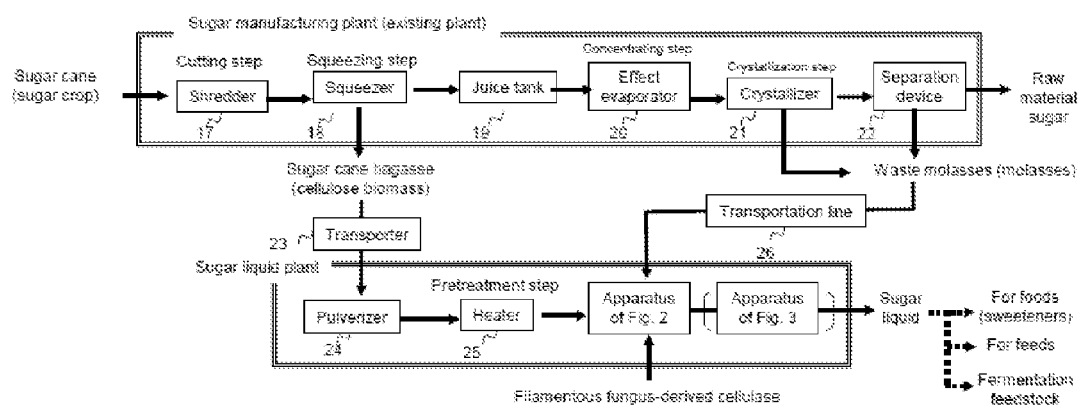
FIG. 5 is a schematic diagram showing the constitution of an apparatus in a case where a sugar liquid manufacturing plant comprising the apparatus of FIG. 2 is constructed next to an existing sugar manufacturing plant.

FIG. 5 is a schematic diagram showing the constitution of an apparatus in a case where a sugar liquid plant comprising our sugar liquid manufacturing apparatus is constructed next to an existing sugar manufacturing plant. The diagram shows an example wherein the existing sugar manufacturing plant uses sugar cane as a raw material of sugar. The sugar manufacturing plant comprises a shredder (cutting step) (17) for cutting sugar cane, a squeezer (squeezing step) (18) that squeezes the sugar cane to obtain sugar cane juice, a juice tank (19) for storing the sugar cane juice, an effect evaporator (multieffect evaporator) (20) that concentrates the sugar cane juice (concentrating step), a crystallizer (21) that crystallizes the sugar contained in the concentrate (crystallization step), and a separation device (22) that separates the crystallized raw material sugar. The waste molasses to be used is discharged from the crystallizer (21) or the separation device (22). The sugar cane bagasse discharged from the squeezer (18) is transported by a transporter (23) such as a conveyor to the sugar liquid plant. The sugar cane bagasse is pulverized by a pulverizer (24) at the stage before the pretreatment step. As the pulverizer, a grinder mill, cutter mill, hammer mill or the like may be used, or a combination of a plurality of these may be used. The pulverized sugar cane bagasse is pretreated in a heater (25) having at least a heating function (pretreatment step). In the pretreatment, an acid, alkali, dilute sulfuric acid, ammonia, caustic soda or the like may be added as described above. The pretreated product of cellulose is subjected to hydrolysis with filamentous fungus-derived cellulase using the apparatus of FIG. 2 described above (Step 1). Thereafter, the waste molasses (molasses) discharged from the sugar manufacturing plant is added to the hydrolysate of Step (1). The waste molasses is connected to the apparatus of FIG. 2 via a transportation line (26). The apparatus of FIG. 3 for concentrating sugar may be added next to the apparatus of FIG. 2. Further, as described above, the sugar liquid may be used for foods, feeds, fermentation feedstocks and the like.

EXAMPLES

Our methods are described below more specifically by way of Examples. However, this disclosure is not limited to such examples.

Reference Example 1

Preparation of Pretreated Product of Cellulose

Hydrothermal Treatment

As a cellulose-containing biomass, sugar cane bagasse was used. The cellulose-containing biomass was immersed in water, and subjected to treatment using an autoclave (manufactured by Nitto Koatsu Co., Ltd.) with stirring at 180° C. for 20 minutes. After the treatment, solid-liquid separation was carried out by centrifugation (3000 G) to separate the pretreated product of cellulose from the solution component. The pretreated product of cellulose obtained was used in the Examples below.

Reference Example 2

Measurement of Sugar Concentration

The concentrations of sucrose, glucose and xylose contained in the sugar liquid were measured under the HPLC conditions described below based on comparison with standard samples:
Column: Luna $NH_2$ (manufactured by Phenomenex, Inc.)
Mobile phase: MilliQ:acetonitrile=25:75 (flow rate, 0.6 mL/minute)
Reaction solution: None
Detection method: RI (differential refractive index)
Temperature: 30° C.

Reference Example 3

Analysis of Fermentation Inhibitors

Aromatic compounds and furan compounds were quantified under the HPLC conditions described below based on comparison with standard samples. Each analysis sample was centrifuged at 3500 G for 10 minutes, and the obtained supernatant component was subjected to the following analysis:
Column: Synergi HidroRP 4.6 mm×250 mm (manufactured by Phenomenex)
Mobile phase: acetonitrile-0.1% $H_3PO_4$ (flow rate, 1.0 mL/min.)
Detection method: UV (283 nm)
Temperature: 40° C.
Acetic acid and formic acid were quantified under the HPLC conditions described below based on comparison with standard samples. Each analysis sample was centrifuged at 3500 G for 10 minutes, and the obtained supernatant component was subjected to the following analysis:
Column: Shim-Pack and Shim-Pack SCR101H (manufactured by Shimadzu Corporation) that are linearly arranged
Mobile phase: 5 mM p-toluenesulfonic acid (flow rate, 0.8 mL/min.)
Reaction solution: 5 mM p-toluenesulfonic acid, 20 mM Bis-Tris, 0.1 mM
EDTA-2Na (flow rate, 0.8 mL/min.)
Detection method: Electric conductivity
Temperature: 45° C.

Reference Example 4

Preparation of *Trichoderma*-derived Cellulase

*Trichoderma*-derived cellulase was prepared by the following method. Preculture
The mixture of 5% (w/vol) corn steep liquor, 2% (w/vol) glucose, 0.37% (w/vol) ammonium tartrate, 0.14 (w/vol) ammonium sulfate, 0.2% (w/vol) potassium dihydrogen phosphate, 0.03% (w/vol) calcium chloride dihydrate, 0.03% (w/vol) magnesium sulfate heptahydrate, 0.02% (w/vol) zinc chloride, 0.01% (w/vol) iron (III) chloride hexahydrate, 0.004% (w/vol) copper (II) sulfate pentahydrate, 0.0008% (w/vol) manganese chloride tetrahydrate, 0.0006% (w/vol) boric acid and 0.0026% (w/vol) hexaammonium heptamolybdate tetrahydrate in distilled water was prepared, and 100 mL of this mixture was placed in a baffled 500-mL Erlenmeyer flask, followed by being sterilized by autoclaving at 121° C. for 15 minutes. After allowing the mixture to cool, PE-M and Tween 80, each of which was sterilized by autoclaving at 121° C. for 15 minutes separately from the mixture, were added thereto at 0.01% (w/vol) each. To this preculture medium, *Trichoderma reesei* PC3-7 was inoculated at 1×10$^5$ cells/mL, and the cells were cultured at 28° C. for 72 hours with shaking at 180 rpm, to perform preculture (shaker: BIO-SHAKER BR-40LF, manufactured by TAITEC CORPORATION).

Main Culture

The mixture of 5% (w/vol) corn steep liquor, 2% (w/vol) glucose, 10% (w/vol) cellulose (Avicel), 0.37% (w/vol) ammonium tartrate, 0.14% (w/vol) ammonium sulfate, 0.2% (w/vol) potassium dihydrogen phosphate, 0.03% (w/vol) calcium chloride dihydrate, 0.03% (w/vol) magnesium sulfate heptahydrate, 0.02% (w/vol) zinc chloride, 0.01% (w/vol) iron (III) chloride hexahydrate, 0.004% (w/vol) copper (II) sulfate pentahydrate, 0.0008% (w/vol) manganese chloride tetrahydrate, 0.0006% (w/vol) boric acid and 0.0026% (w/vol) hexaammonium heptamolybdate tetrahydrate in distilled water was prepared, and 2.5 L of this mixture was placed in a 5-L stirring jar (manufactured by ABLE, DPC-2A), followed by being sterilized by autoclaving at 121° C. for 15 minutes. After allowing the mixture to cool, PE-M and Tween 80, each of which was sterilized by autoclaving at 121° C. for 15 minutes separately from the mixture, were added thereto at 0.1% each. To the resulting mixture, 250 mL of the preculture of *Trichoderma reesei* PC3-7 preliminarily prepared with a liquid medium by the method described above was inoculated. The cells were then cultured at 28° C. for 87 hours at 300 rpm at an aeration rate of 1 vvm. After centrifugation, the supernatant was subjected to membrane filtration (Stericup-GV, manufactured by Millipore, material: PVDF). To the culture liquid prepared under the above-described conditions, β-glucosidase (Novozyme 188) was added at a protein weight ratio of 1/100, and the resulting mixture was used as the *Trichoderma*-derived cellulase in the Examples below.

Reference Example 5

Method for Measuring Amount of Filamentous Fungus-derived Cellulase Recovered

The amount of the filamentous fungus-derived cellulase that could be recovered in Step (3) was quantified by measuring 3 kinds of degradation activities (hereinafter referred to as activity values): 1) crystalline cellulose-degrading activity; 2) cellobiose-degrading activity; and 3) xylan-degrading activity.

1) Crystalline Cellulose-Degrading Activity

To an enzyme liquid (prepared under predetermined conditions), a crystalline cellulose Avicel (Cellulose Microcrystalline, manufactured by Merch) was added at 1 g/L and sodium acetate buffer (pH 5.0) was added at 100 mM, followed by allowing the resulting mixture to react at 50° C. for 24 hours. This reaction liquid was prepared in a 1-mL tube, and the reaction was allowed to proceed with mixing by rotation under the above-described conditions. Thereafter, the tube was subjected to centrifugation, and the glucose concentration in the supernatant component was measured. The measurement of glucose concentration was carried out according to the method described in Reference Example 2. The concentration of glucose produced (g/L) was used as it is as the activity level of the crystalline cellulose-degrading activity, and used for comparison of the amount of enzyme recovered.

2) Cellobiose-Degrading Activity

To an enzyme liquid, cellobiose (Wako Pure Chemical Industries, Ltd.) was added at 500 mg/L and sodium acetate buffer (pH 5.0) was added at 100 mM, followed by allowing the resulting mixture to react at 50° C. for 0.5 hour. This reaction liquid was prepared in a 1-mL tube, and the reaction was allowed to proceed with mixing by rotation under the above-described conditions. Thereafter, the tube was subjected to centrifugation, and the glucose concentration in the supernatant component was measured. The measurement of glucose concentration was carried out according to the method described in Reference Example 2. The concentration of glucose produced (g/L) was used as it is as the activity level of the cellobiose-degrading activity, and used for comparison of the amount of enzyme recovered.

3) Xylan-Degrading Activity

To an enzyme liquid, xylan (Birch wood xylan, Wako Pure Chemical Industries, Ltd.) was added at 10 g/L and sodium acetate buffer (pH 5.0) was added at 100 mM, followed by allowing the resulting mixture to react at 50° C. for 4 hours. This reaction liquid was prepared in a 1-mL tube, and the reaction was allowed to proceed with mixing by rotation under the above-described conditions. Thereafter, the tube was subjected to centrifugation, and the xylose concentration in the supernatant component was measured. The measurement of xylose concentration was carried out according to the method described in Reference Example 2. The concentration of xylose produced (g/L) was used as it is as the activity level of the xylose-degrading activity, and used for comparison of the amount of enzyme recovered.

Reference Example 6

Measurement of Inorganic Ion Concentration

The concentrations of cations and anions contained in the sugar liquid were quantified under the HPLC conditions shown below based on comparison with standard samples.

1) Cation Analysis

Column: Ion Pac AS22 (manufactured by DIONEX)
Mobile phase: 4.5 mM $Na_2CO_3$/1.4 mM $NaHCO_3$ (flow rate, 1.0 mL/minute)
Reaction solution: None
Detection method: Electric conductivity (by use of a suppressor)
Temperature: 30° C.

2) Anion Analysis

Column: Ion Pac CS12A (manufactured by DIONEX)
Mobile phase: 20 mM Methanesulfonic acid (flow rate, 1.0 mL/minute)
Reaction solution: None
Detection method: Electric conductivity (by use of a suppressor)
Temperature: 30° C.

Reference Example 7

Analysis of Components of Waste molasses

As a waste molasses, "waste molasses (Molasses Agri)" (manufactured by Organic Land Co., Ltd.) was used. The raw material of the waste molasses was raw sugar derived from sugar cane. The results of analysis of sugar components, organic acids, aromatic/furan compounds and inorganic ions in the waste molasses are shown in Tables 1 to 4. The total concentration of each group of components is shown in Table 5. The analysis of components was carried out according to Reference Example 2, Reference Example 3 and Reference Example 6.

TABLE 1

| Sugar components | | | | |
|---|---|---|---|---|
| Component name | Glucose | Xylose | Sucrose | Fructose |
| Concentration (g/L) | 148 | 6 | 371 | 164 |

TABLE 2

| Organic acid components | | |
|---|---|---|
| Component name | Acetic acid | Formic acid |
| Concentration (g/L) | 0.3 | 0 |

TABLE 3

| Aromatic/furan compounds | | | | | |
|---|---|---|---|---|---|
| | Component name | | | | |
| | HMF*1 | Furfural | Coumaric acid | Ferulic acid | Vanillin |
| Concentration (mg/L) | 116 | 3.5 | 24 | 17 | 7.0 |
| | Component name | | | | |
| | Acetovanillin | | Coniferyl aldehyde | | Guaiacol |
| Concentration (mg/L) | 9.6 | | 7.6 | | 339 |

*1hydroxymethylfurfural

TABLE 4

| Inorganic ions | | | | |
|---|---|---|---|---|
| Component name | $K^+$ ion | $Mg^{2+}$ ion | $Ca^{2+}$ ion | $Na^+$ ion |
| Concentration (g/L) | 11.8 | 0.71 | 1.3 | 0.67 |
| Component name | $NH_4^-$ ion | $Cl^-$ ion | $PO_4^-$ ion | $SO_4^{-2}$ ion |
| Concentration (g/L) | 0.21 | 0.2 | 0 | 0.23 |

TABLE 5

| Total concentration of each component group | | | | |
|---|---|---|---|---|
| | Component name | | | |
| | Sugars | Organic acids | Aromatic/furan Compounds | Inorganic ions |
| Concentration (g/L) | 689 | 3.3 | 0.5 | 15 |

Reference Example 8

Analysis of Ethanol Concentration

The concentration of ethanol accumulated was quantified by gas chromatography. Its evaluation was carried out by detection and calculation with a hydrogen salt ionization detector using Shimadzu GC-2010 Capillary GC TC-1 (GL Science) 15 meter L.×0.53 mm I. D., df 1.5 μm.

Comparative Example 1

Production of Sugar Liquid without Addition of Waste molasses to Hydrolysate

Step (1):

To the pretreated product of cellulose (0.5 g) prepared in Reference Example 1, distilled water was added, and 0.5 mL of the *Trichoderma*-derived cellulase prepared in Reference Example 4 was added, followed by further adding distilled water to a total weight of 10 g. Thereafter, dilute sulfuric acid or dilute caustic soda was added to the resulting composition such that the pH of the composition was within the range of 4.5 to 5.3. After the pH adjustment, the composition was transferred to a side-arm test tube (manufactured by Tokyo Rikakikai Co., Ltd., φ30 NS14/23, compact mechanical stirrer CPS-1000, conversion adapter, feed inlet with a three-way stopcock, incubator MG-2200), and incubated and stirred at 50° C. for 24 hours to obtain a hydrolysate.

Step (2):

Step (2) was not carried out in this Comparative Example.

Step (3):

The hydrolysate obtained in Step (1) was subjected to solid-liquid separation by centrifugation (3000 G, 10 minutes), and thereby separated into the solution component (6 mL) and solids. The solution component was further filtered using a Millex HV filter unit (33 mm; made of PVDF; pore size, 0.45 μm). Sugar concentrations (glucose and xylose concentrations) in the obtained solution component were measured according to the method described in Reference Example 2. The measured sugar concentrations are shown in Table 6. The obtained solution component was filtered through an ultrafiltration membrane having a molecular weight cutoff of 10000 (VIVASPIN 20, manufactured by Sartorius stedim biotech, material: PES) and centrifuged at 4500 G until the membrane fraction was reduced to 1 mL. To the membrane fraction, 10 mL of distilled water was added, and the resulting mixture was centrifuged again at 4500 G until the membrane fraction was reduced to 1 mL. This operation was carried out once again, and the recovered enzyme liquid was collected from the membrane fraction. The amount of enzyme recovered was quantified by measuring each activity value according to Reference Example 5

The activity value measured in the present Comparative Example 1 was defined as "1 (reference)," and used for comparison with the amounts of recovered enzyme in the later-described Comparative Example 2 and Example 1 (Table 7).

Comparative Example 2

Production of Sugar Liquid by Addition of Reagent Sugar Liquid

Step (1):

Step (1) was carried out by the same procedure as in Step (1) of Comparative Example 1.

Step (2):

A reagent sugar liquid, which is not waste molasses, was added to the hydrolysate of Step (1). The reagent sugar liquid was prepared such that the sugar concentrations were the same as those in the waste molasses described in Reference Example 7. That is, the reagent sugar liquid was prepared by completely dissolving 148 g of glucose, 163 g of fructose and 371 g of sucrose in 1 L of RO water. To the hydrolysate of Step (1), 0.5 mL of the thus obtained reagent sugar liquid was added. Thereafter, the resulting mixture was stirred at room temperature (25° C.) for about 5 minutes to prepare a mixed sugar liquid as a uniform liquid.

Step (3):

The mixed sugar liquid obtained in Step (2) was used for carrying out solid-liquid separation and ultrafiltration membrane treatment by the same procedure as in Step (3) of Comparative Example 1. The concentrations of sugars obtained are shown in Table 6. Each measured activity value was divided by the activity value of Comparative Example 1. The obtained value is shown in Table 7 as the amount of recovered enzyme of Comparative Example 2.

Example 1

Method of Preparing Sugar Liquid by Adding Waste molasses to Cellulose Hydrolysate Step (1):

Step (1) was carried out by the same procedure as in Step (1) of Comparative Example 1.

Step (2):

To the hydrolysate (10 mL) obtained in Step (1), 0.5 g of waste molasses (Reference Example 7; sugar concentration, 689 g/L) was added. Thereafter, the resulting mixture was stirred at room temperature (25° C.) for about 5 minutes to prepare a mixed sugar liquid as a uniform liquid.

Step (3):

Using the mixed sugar liquid obtained in Step (2), solid-liquid separation and ultrafiltration membrane treatment were carried out by the same procedure as in Step (3) of Comparative Example 1. The concentrations of sugars obtained are shown in Table 6. Each measured activity value was divided by the activity value of Comparative Example 1. The obtained value is shown in Table 7 as the amount of recovered enzyme of Example 1.

Based on comparison among Comparative Example 1, Comparative Example 2 and Example 1, the amount of recovered enzyme was higher in Example 1 than in Comparative Example 1, so that it was suggested that waste molasses contains a component that increases the amount of recovered enzyme. Further, since the amount of recovered enzyme of Reference Example 2 was almost the same as that of Reference Example 1, it was suggested that the sugar components contained in the waste molasses (sucrose, glucose and fructose) do not affect the amount of recovered enzyme and that another component is involved in the increased recovery of enzyme.

TABLE 6

| | Sugar concentration | | | | |
|---|---|---|---|---|---|
| | Glucose (g/L) | Xylose (g/L) | Sucrose (g/L) | Fructose (g/L) | Total sugar (g/L) |
| Comparative Example 1 | 16 | 9.5 | 0 | 0 | 25.5 |
| Comparative Example 2 | 22.2 | 9.3 | 17.7 | 7.8 | 57 |
| Example 1 | 22.2 | 9.3 | 17.7 | 7.8 | 57 |

TABLE 7

| | Amount of recovered enzyme (relative value) | | |
|---|---|---|---|
| | Crystalline cellulose-degrading activity | Xylan-degrading activity | Cellobiose-degrading activity |
| Comparative Example 1 | 1 (Reference) | 1 (Reference) | 1 (Reference) |
| Comparative Example 2 | 1.2 | 0.8 | 1.3 |
| Example 1 | 2.8 | 2.1 | 1.5 |

Example 2

Relationship Between Amount of Waste Molasses Added and Amount of Recovered Enzyme Step (2) was carried out in the same manner as in Example 1 except that the waste molasses was added in an amount of 0.1 g (Example 1), 0.5 g, 1 g, 2 g or 5 g, and the amount of filamentous fungus-derived cellulase that could be recovered was compared. Each activity value of recovered enzyme in each experimental group was divided by the activity value of Comparative Example 1. The obtained value is shown in Table 8 as the amount of recovered enzyme (relative value). As a result, it was found that, as the amount of waste molasses added increases, the amount of recovered enzyme, especially the amount of enzyme involved in the crystalline cellulose-degrading activity, increases.

TABLE 8

| | Relationship between the amount of waste molasses added and the amount of recovered enzyme (relative value) | | |
|---|---|---|---|
| | Crystalline cellulose-degrading activity | Xylan-degrading activity | Cellobiose-degrading activity |
| Comparative Example 1 | 1 (Reference) | 1 (Reference) | 1 (Reference) |
| 0.5 g (Example 1) | 2.8 | 2.1 | 1.5 |
| 1 g | 3.4 | 2.3 | 1.5 |
| 2 g | 3.8 | 2.8 | 1.5 |
| 5 g | 5.2 | 2.8 | 1.8 |

Comparative Example 3

Relationship Between Amount of Reagent Sugar Added and Amount of Recovered Enzyme Step (2) was carried out in the same manner as in Comparative Example 2 except that the reagent sugar liquid was added in an amount of 0.1 g (Comparative Example 2), 0.5 g, 1 g, 2 g or 5 g, and the amount of filamentous fungus-derived cellulase that could be recovered was compared. As a result, it was found as shown in Table 9 that, unlikely to the result of Example 2, the amount of recovered enzyme does not increase in terms of any of the activities even if the amount of reagent sugar added increases. That is, it was found that a component other than the sugars contained in the waste molasses is involved in the increased amount of recovered enzyme.

TABLE 9

Relationship between the amount of reagent sugar
added and the amount of recovered enzyme

|  | Crystalline cellulose-degrading activity | Xylan-degrading activity | Cellobiose-degrading activity |
|---|---|---|---|
| Comparative Example 1 | 1 (Reference) | 1 (Reference) | 1 (Reference) |
| 0.5 g (Comparative Example 2) | 1.1 | 0.9 | 1.1 |
| 1 g | 1.2 | 0.8 | 1.3 |
| 2 g | 1.1 | 0.8 | 1.1 |
| 5 g | 1.3 | 0.8 | 1.1 |

Example 3

Relationship Between Incubation Temperature of Mixed Sugar Liquid and Amount of Enzyme Recovered Step (2) was carried out in the same manner as in Example 1 except that the temperature of incubation after the addition of 0.5 g of waste molasses to prepare a mixed sugar liquid was set to 25° C. (Example 1), 40° C., 50° C., 60° C. or 70° C. The activity values of the recovered enzyme were measured for comparison of the amount of recovered enzyme among the experimental groups (Table 10). As a result, it was found that incubation of the mixed sugar liquid within the temperature range of 40 to 60° C. further increases the amount of recovered enzyme.

TABLE 10

Relationship between the incubation temperature of the
mixed sugar liquid and the amount of enzyme recovered

| Incubation temperature | Crystalline cellulose-Degrading activity | Xylan-degrading activity | Cellobiose-degrading activity |
|---|---|---|---|
| (Comparative Example 1) | 1 (Reference) | 1 (Reference) | 1 (Reference) |
| 25° C. (Example 1) | 2.8 | 2.1 | 1.5 |
| 40° C. | 3.3 | 2.8 | 1.5 |
| 50° C. | 3.8 | 2.8 | 1.5 |
| 60° C. | 3.2 | 2.1 | 1.8 |
| 70° C. | 2.1 | 1.2 | 1.5 |

Example 4

Step of Obtaining Concentrated Sugar Liquid Using Nanofiltration Membrane or Reverse Osmosis Membrane Preparation of Sugar Liquid A sugar liquid (1 L) was prepared under the following conditions.

Step (1):

To the pretreated product of cellulose (400 g) obtained in Reference Example 1, 4 g of *Trichoderma*-derived cellulase was added, and distilled water was further added to a total weight of 8 kg. Further, the pH of the composition was adjusted with dilute caustic soda to a value within the range of 4.5 to 5.3. While the liquid was incubated such that a liquid temperature of 45 to 50° C. was maintained, and while dilute sulfuric acid and/or dilute caustic soda was/were added to the liquid such that the pH was maintained within the range of 4.5 to 5.3, the liquid was incubated for 24 hours, to obtain 8 kg of a hydrolysate.

Step (2):

To 8 kg of the hydrolysate obtained in Step (1), 0.4 kg of waste molasses was added. Thereafter, the resulting mixture was mixed for 5 minutes to obtain a mixed sugar liquid as a uniform liquid.

Step (3)

The mixed sugar liquid obtained in Step (2) was subjected to solid-liquid separation and ultrafiltration membrane treatment. For the solid-liquid separation, a compact filter press apparatus (filter press MO-4, manufactured by Yabuta Industries Co., Ltd.) was used. As a filter cloth, a polyester woven fabric (T2731C, manufactured by Yabuta Industries Co., Ltd.) was used. In a small tank, 8 L of the mixed sugar liquid was placed. Under aeration with compressed air from the bottom, a liquid inlet was opened to feed the slurry liquid slowly to a filtration chamber using an air pump (66053-3EB, manufactured by Taiyo International Corporation). Subsequently, a compression step was carried out by swelling a diaphragm attached to the filtration chamber. The compression pressure was slowly increased to 0.5 MPa, and the apparatus was then left to stand for about 30 minutes to recover the solution component as a filtrate. The total volume of the solution component obtained was 6 L. The remaining liquid component was lost because of the dead volume of the apparatus. Subsequently, the solution component after solid-liquid separation was filtered through a microfiltration membrane. The microfiltration was carried out using Stericup HV 1000 mL (manufactured by Millipore; PVDF; average pore size, 0.45 μm), to obtain 5 L of a filtrate. The obtained filtrate (solution component) was processed using a compact flat membrane filtration device (Sepa (registered trademark) CF II Med/High Foulant System, manufactured by GE) equipped with a flat ultrafiltration membrane having a molecular weight cutoff of 10000 (SEPA PW series, manufactured by GE, material of the functional surface: polyether sulfone). While the operating pressure was controlled such that the flow rate in the feed side was constantly 2.5 L/minute and the membrane flux was constantly 0.1 m/D, 4 L out of 5 L of the above filtrate was filtered, to obtain a sugar liquid.

Treatment of Sugar Liquid Using Nanofiltration Membrane or Reverse Osmosis Membrane Using 1 L of the sugar liquid produced in the Steps (1) to (3), concentration through a nanofiltration membrane or concentration through a reverse osmosis membrane was carried out. As the nanofiltration membrane, "DESAL-5L" (manufactured by Desalination) was used. As the reverse osmosis membrane, a cross-linked wholly aromatic reverse osmosis membrane "UTC80" (manufactured by Toray Industries, Inc.) was used. Each membrane was mounted on a compact flat membrane filtration device ("Sepa" (registered trademark) CF II Med/High Foulant System, manufactured by GE), and filtration treatment was carried out at a raw liquid temperature of 25° C. at a pressure of 3 MPa using a high-pressure pump. By this treatment, 0.5 L of a nanofiltration membrane concentrate and 0.5 L of a permeate were obtained (2-fold concentration). The concentrated sugar liquid obtained using the nanofiltration membrane is shown in Table 11, and the concentrated sugar liquid obtained using the reverse osmosis membrane is shown in Table 12. As shown in Table 11 and Table 12, it was found that, although concentration of sugar components is possible with either a nanofiltration membrane or a reverse osmosis membrane, concentration through a nanofiltration membrane has higher effect of removing fermentation inhibitors such as HMF, furfural, acetic acid and potassium ions.

TABLE 11

Concentrated sugar liquid prepared with a nanofiltration membrane

|  | Sugar liquid | Concentrated sugar liquid | Permeate |
|---|---|---|---|
| Glucose (g/L) | 26 | 50 | 2.0 |
| Xylose (g/L) | 2.2 | 4.1 | 0.42 |
| Sucrose (g/L) | 17 | 33 | 0.11 |
| Fructose (g/L) | 7.8 | 15.5 | 0.0 |
| Acetic acid (g/L) | 0.62 | 0.65 | 0.50 |
| HMF (mg/L) | 86 | 90 | 80 |
| Furfural (mg/L) | 300 | 310 | 290 |
| Coumaric acid (mg/L) | 6.2 | 9.6 | 2.8 |
| Ferulic acid (mg/L) | 3.8 | 6.9 | 0.50 |
| Vanillin (mg/L) | 7.7 | 9.2 | 6.2 |
| Acetovanillin (mg/L) | 1.3 | 2.5 | 0.11 |
| Coniferyl aldehyde (mg/L) | 0.91 | 1.2 | 0.61 |
| Guaiacol (mg/L) | 18 | 34 | 2.2 |
| Potassium ion (g/L) | 0.61 | 0.92 | 0.33 |

TABLE 12

Concentrated sugar liquid prepared with a reverse osmosis membrane

|  | Sugar liquid | Concentrated sugar liquid | Permeate |
|---|---|---|---|
| Glucose (g/L) | 26 | 52 | 0.22 |
| Xylose (g/L) | 2.2 | 4.4 | 0.13 |
| Sucrose (g/L) | 17 | 34 | 0.0 |
| Fructose (g/L) | 7.8 | 16 | 0.0 |
| Acetic acid (g/L) | 0.62 | 1.2 | 0.0 |
| HMF (mg/L) | 86 | 170 | 2.1 |
| Furfural (mg/L) | 300 | 590 | 0.20 |
| Coumaric acid (mg/L) | 6.2 | 12 | 0.13 |
| Ferulic acid (mg/L) | 3.8 | 7.5 | 0.0 |
| Vanillin (mg/L) | 7.7 | 15 | 0.15 |
| Acetovanillin (mg/L) | 1.3 | 2.6 | 0.0 |
| Coniferyl aldehyde (mg/L) | 0.91 | 1.9 | 0.0 |
| Guaiacol (mg/L) | 18 | 36 | 0.0 |
| Potassium ion (g/L) | 0.61 | 1.1 | 0.0 |

Example 5

Ethanol Fermentation Test Using Sugar Liquid as Fermentation Feedstock

Using the sugar liquid obtained by the sugar liquid preparation process of Example 4 (carried out by Steps (1) to (3)) and using an yeast (*Saccharomyces cerevisiae* OC-2: wine yeast), an ethanol fermentation test was carried out. For comparison, a mixed sugar liquid obtained by carrying out Steps (1) and (2) of the sugar liquid preparation process of Example 4 was also used as a fermentation feedstock. The yeast was precultured in YPD medium (2% glucose, 1% yeast extract (Bacto Yeast Extract, manufactured by BD), 2% polypeptone (manufactured by Nihon Pharmaceutical Co., Ltd.)) for 1 day at 25° C. Subsequently, the obtained culture liquid was added to the sugar liquid or the mixed sugar liquid (sugar concentration, 57 g/L) at a concentration of 1% (20 mL). After the addition of the microorganism, incubation was performed at 25° C. for 2 days. The culture liquid obtained by this operation was subjected to analysis of the concentration of accumulated ethanol by the procedure of Reference Example 8. As shown in Table 13, it was found that direct use of a mixed sugar liquid prepared by only mixing a cellulose hydrolysate with waste molasses results in low concentration of accumulated ethanol. This was assumed to be due to the action of substances that should be removed in Step (3) as fermentation inhibition factors.

TABLE 13

Ethanol fermentation test

| Fermentation feedstock | Concentration of ethanol accumulated (g/L) |
|---|---|
| Mixed sugar liquid: obtained by carrying out Steps (1) and (2) | 9 g/L |
| Sugar liquid: obtained by carrying out Steps (1) to (3) | 13 g/L |

Example 6

Ethanol Fermentation Test Using Concentrated Sugar Liquid as Fermentation Feedstock The concentrated sugar liquid prepared using a nanofiltration membrane and the concentrated sugar liquid prepared using a reverse osmosis membrane in Example 4 were diluted 2-fold with RO water, and used as fermentation media by the same procedure as in Example 5. As a result, as shown in Table 14, both concentrated sugar liquids showed higher fermentation performance than the sugar liquid of Example 5, and it was found that a concentrated sugar liquid prepared using a nanofiltration membrane is especially excellent as a fermentation medium.

TABLE 14

Ethanol fermentation test

| Fermentation feedstock | Concentration of ethanol accumulated (g/L) |
|---|---|
| Nanofiltration membrane-concentrated sugar liquid | 19 g/L |
| Reverse osmosis membrane-concentrated sugar liquid | 15 g/L |

Example 7

Invertase Treatment of Mixed Sugar Liquid

To the hydrolysate (10 mL) of Step (2) of Example 1, 0.5 g of waste molasses (Reference Example 7; sugar concentration, 689 g/L) was added. Thereafter, the resulting mixture was stirred at room temperature (50° C.) for about 5 minutes to prepare a mixed sugar liquid as a uniform liquid. Subsequently, 1 g of yeast-derived invertase (Invertase solution, from yeast; Wako Pure Chemical Industries, Ltd.) was added to the mixed sugar liquid, and the resulting mixture was left to stand for additional 1 hour.

Step (3)

Using the mixed sugar liquid obtained in Step (2), solid-liquid separation and ultrafiltration membrane treatment were carried out by the same procedure as in Step (3) of Comparative Example 1. The concentrations of sugars obtained are shown in Table 15.

TABLE 15

| | Sugar concentrations | | | | |
|---|---|---|---|---|---|
| | Glucose (g/L) | Xylose (g/L) | Sucrose (g/L) | Fructose (g/L) | Total sugar (g/L) |
| Example 7 | 31.0 | 9.3 | 0.2 | 17 | 57 |

As shown in Table 15, it was found that, because of hydrolysis of sucrose, the sugar concentrations of glucose and fructose increase compared to their concentrations in Example 1.

Example 8

L-Lactic Acid Production Using Sugar Liquid Treated with Invertase

The *Lactococcus lactis* JCM7638 strain was inoculated to 5 mL of the sugar liquid of Example 7, and static culture was carried out for 24 hours at a temperature of 37° C. The L-lactic acid concentration in the culture liquid was analyzed under the following conditions.

Column: Shim-Pack SPR-H (manufactured by Shimadzu Corporation)
Mobile phase: 5 mM p-toluenesulfonic acid (flow rate, 0.8 mL/min.)
Reaction solution: 5 mM p-toluenesulfonic acid, 20 mM Bis-Tris, 0.1 mM
EDTA-2Na (flow rate, 0.8 mL/min.)
Detection method: Electric conductivity
Temperature: 45° C.

As a result of the analysis, accumulation of 26 g/L L-lactic acid was found, and it could be confirmed that lactic acid can be produced using the sugar liquid from our method.

Comparative Example 4

L-Lactic Acid Production Using Reagent Sugar Liquid

For comparison, glucose, xylose, sucrose and fructose were mixed together such that the sugar concentrations described in Table 15 were attained, to prepare 5 mL of a reagent sugar liquid. The *Lactococcus lactis* JCM7638 strain was inoculated to the reagent sugar liquid, and static culture was carried out for 24 hours at a temperature of 37° C. However, no growth could be observed. This was considered to be due to the absence, unlike the sugar liquid of Example 8, of amino acids, vitamins and the like for growth of the lactic acid bacterium in the reagent sugar liquid.

Reference Example 9

As the cellulose-containing biomass, sugar cane bagasse was used. The cellulose-containing biomass was immersed in 1% aqueous sulfuric acid solution, and subjected to treatment using an autoclave (manufactured by Nitto Koatsu Co., Ltd.) at 150° C. for 30 minutes. Thereafter, solid-liquid separation was carried out to separate the resultant into an aqueous sulfuric acid solution (hereinafter referred to as dilute-sulfuric-acid-treated liquid) and a pretreated product of cellulose (dilute sulfuric acid).

Comparative Example 5

Production of Sugar Liquid without Addition of Waste molasses to Hydrolysate

Using the pretreated product of cellulose (dilute sulfuric acid) prepared in Reference Example 9, a recovered enzyme liquid was collected by the same procedure as in Comparative Example 1. The amount of enzyme recovered was quantified by measuring each activity value according to Reference Example 5. The activity value measured in the present Comparative Example 5 was defined as "1 (reference)", and used for comparison with the amounts of recovered enzyme in the later-described Comparative Example 6 and Example 9 (Table 16).

Comparative Example 6

Production of Sugar Liquid with Addition of Reagent Sugar Liquid to Hydrolysate

Step (1):
Step (1) was carried out by the same procedure as in Step (1) of Comparative Example 1.
Step (2):
Step (2) was carried out by the same procedure as in Comparative Example 2.
Step (3):
Using the mixed sugar liquid obtained in Step (2), solid-liquid separation and ultrafiltration membrane treatment were carried out by the same procedure as in Step (3) of Comparative Example 1. Each measured activity value was divided by the activity value of Comparative Example 5. The obtained value is shown in Table 16 as the amount of recovered enzyme of Comparative Example 6.

Example 9

Method of Producing Sugar Liquid with Addition of Waste molasses to Cellulose Hydrolysate Step (1):
Step (1) was carried out by the same procedure as in the Step (1) of Comparative Example 1.
Step (2):
Step (2) was carried out by the same procedure as in Example 1.
Step (3):
Using the mixed sugar liquid obtained in Step (2), solid-liquid separation and ultrafiltration membrane treatment were carried out by the same procedure as in Step (3) of Comparative Example 1. Each measured activity value was divided by the activity value of Comparative Example 5. The obtained value is shown in Table 16 as the amount of recovered enzyme of Example 9.

Based on comparison among Comparative Example 5, Comparative Example 6 and Example 9, the amount of recovered enzyme was higher in Example 9 than in Comparative Example 5, so that it was suggested that waste molasses contains a component that increases the amount of recovered enzyme. Further, since the amount of recovered enzyme of Comparative Example 6 was almost the same as that of Comparative Example 5, it was suggested that the sugar components contained in the waste molasses (sucrose, glucose and fructose) do not affect the amount of recovered enzyme and that another component is involved in the increased recovery of enzyme. These results indicate that waste molasses increases the activities of recovered enzyme, irrespective of whether the cellulose was pretreated or not.

TABLE 16

| Amount of recovered enzyme 2 (relative value) | | | |
|---|---|---|---|
| | Crystalline cellulose-Egrading activity | Xylan-degrading activity | Cellobiose-degrading activity |
| Comparative Example 5 | 1 (Reference) | 1 (Reference) | 1 (Reference) |
| Comparative Example 6 | 0.9 | 0.7 | 1.2 |
| Example 9 | 4.8 | 5.1 | 2.5 |

INDUSTRIAL APPLICABILITY

Our methods enable production of a sugar liquid from cellulose-containing biomass, which sugar liquid can be used as a fermentation feedstock for fermentation production of various chemical products.

The invention claimed is:

1. A method for producing a sugar liquid, said method comprising:
   (1) adding a filamentous fungus-derived cellulase to a pretreated product of cellulose to obtain a hydrolysate;
   (2) adding waste molasses to said hydrolysate to obtain a mixed sugar liquid; and
   (3) subjecting said mixed sugar liquid to solid-liquid separation and filtering the obtained solution component through an ultrafiltration membrane to recover the filamentous fungus-derived cellulase as a non-permeate and to obtain a sugar liquid as a permeate.

2. The method according to claim 1, wherein said filamentous fungus-derived cellulase of (1) is *Trichoderma*-derived cellulase.

3. The method according to claim 1, wherein said pretreated product of cellulose of (1) is one or more products selected from the group consisting of products obtained by hydrothermal treatment, dilute sulfuric acid treatment or alkali treatment.

4. The method according to claim 1, wherein, in (2), waste molasses is added to said hydrolysate to prepare a mixed sugar liquid whose sugar concentration is 40 to 200 g/L.

5. The method according to claim 1, wherein (2) comprises a process of incubating said mixed sugar liquid at a temperature of 40 to 60° C.

6. The method according to claim 1, further comprising filtering said sugar liquid of (3) through a nanofiltration membrane and/or reverse osmosis membrane to remove fermentation inhibitors as a permeate and to obtain a sugar concentrate as a non-permeate.

7. A method of producing a chemical product comprising producing a sugar liquid according to claim 1, and culturing a microorganism having a capacity to produce a chemical product using the sugar liquid as a fermentation feedstock.

8. The method according to claim 2, wherein said pretreated product of cellulose of (1) is one or more products selected from the group consisting of products obtained by hydrothermal treatment, dilute sulfuric acid treatment or alkali treatment.

9. The method according to claim 2, wherein, in (2), waste molasses is added to said hydrolysate to prepare a mixed sugar liquid whose sugar concentration is 40 to 200 g/L.

10. The method according to claim 3, wherein, in (2), waste molasses is added to said hydrolysate to prepare a mixed sugar liquid whose sugar concentration is 40 to 200 g/L.

11. The method according to claim 2, wherein (2) comprises a process of incubating said mixed sugar liquid at a temperature of 40 to 60° C.

12. The method according to claim 3, wherein (2) comprises a process of incubating said mixed sugar liquid at a temperature of 40 to 60° C.

13. The method according to claim 4, wherein (2) comprises a process of incubating said mixed sugar liquid at a temperature of 40 to 60° C.

14. The method according to claim 2, further comprising filtering said sugar liquid of (3) through a nanofiltration membrane and/or reverse osmosis membrane to remove fermentation inhibitors as a permeate and to obtain a sugar concentrate as a non-permeate.

15. The method according to claim 3, further comprising filtering said sugar liquid of (3) through a nanofiltration membrane and/or reverse osmosis membrane to remove fermentation inhibitors as a permeate and to obtain a sugar concentrate as a non-permeate.

16. The method according to claim 4, further comprising filtering said sugar liquid of (3) through a nanofiltration membrane and/or reverse osmosis membrane to remove fermentation inhibitors as a permeate and to obtain a sugar concentrate as a non-permeate.

17. The method according to claim 5, further comprising filtering said sugar liquid of (3) through a nanofiltration membrane and/or reverse osmosis membrane to remove fermentation inhibitors as a permeate and to obtain a sugar concentrate as a non-permeate.

18. A method of producing a chemical product comprising producing a sugar liquid according to claim 2, and culturing a microorganism having a capacity to produce a chemical product using the sugar liquid as a fermentation feedstock.

19. A method of producing a chemical product comprising producing a sugar liquid according to claim 3, and culturing a microorganism having a capacity to produce a chemical product using the sugar liquid as a fermentation feedstock.

20. A method of producing a chemical product comprising producing a sugar liquid according to claim 4, and culturing a microorganism having a capacity to produce a chemical product using the sugar liquid as a fermentation feedstock.

* * * * *